United States Patent [19]

Pedersen et al.

[11] Patent Number: 5,405,414
[45] Date of Patent: Apr. 11, 1995

[54] REMOVAL OF PRINTING PASTE THICKENER AND EXCESS DYE AFTER TEXTILE PRINTING

[75] Inventors: Gitte Pedersen, Frederiksberg C; Hans A. Hagen, Farum; Lars Asferg, Gentofte; Ebbe Sørensen, Albertslund, all of Denmark

[73] Assignee: Novo Nordisk A/S, Bagsvaerd, Denmark

[21] Appl. No.: 117,049

[22] PCT Filed: Mar. 13, 1992

[86] PCT No.: PCT/DK92/00078

§ 371 Date: Sep. 9, 1993

§ 102(e) Date: Sep. 9, 1993

[87] PCT Pub. No.: WO92/16685

PCT Pub. Date: Oct. 1, 1992

[30] Foreign Application Priority Data

Mar. 19, 1991 [EP] European Pat. Off. ............ 91610019
Dec. 5, 1991 [EP] European Pat. Off. ............ 91610093

[51] Int. Cl.⁶ ............................................. C09B 67/00
[52] U.S. Cl. ....................................... 8/401; 252/174.12
[58] Field of Search ........................ 8/401; 252/174.12

[56] References Cited

U.S. PATENT DOCUMENTS

| | | | |
|---|---|---|---|
| 3,813,342 | 5/1974 | Cooperman | 252/170 |
| 4,832,864 | 5/1989 | Olson | 252/174 |
| 4,863,483 | 9/1989 | Donenfeld et al. | 8/496 |
| 5,246,853 | 9/1993 | Clarkson et al. | 435/263 |

FOREIGN PATENT DOCUMENTS

| | | |
|---|---|---|
| 2404672 | 9/1978 | France . |
| 2732322 | 2/1979 | Germany . |
| 2168393 | 6/1986 | United Kingdom . |
| WO89/09259 | 10/1989 | WIPO . |
| WO90/07569 | 7/1990 | WIPO . |

OTHER PUBLICATIONS

Udod et al., Chem. Abs., vol. 95, p. 330 (1981) (complete article att.).

*Primary Examiner*—Arthur C. Prescott
*Attorney, Agent, or Firm*—Steve T. Zelson; Elias J. Lambiris

[57] ABSTRACT

In textile printing using a printing paste containing a dye and a biological polymer (or modified polymer) as thickener, removal of the thickener and excess dye is made much more efficient by washing the printed textile in the presence of a suitable enzyme. The enzymatic breakdown of thickener decreases process time as well as the amount of energy and water needed to achieve a satisfactory quality of the textile.

9 Claims, 8 Drawing Sheets

REMOVAL OF PRINTING PASTE THICKENER AND EXCESS DYE AFTER TEXTILE PRINTING

TECHNICAL FIELD

This invention relates to a method for removal of biological polymer or modified polymer and excess dye from printed textile by washing.

BACKGROUND ART

In printing of textiles, it is common to use a printing paste containing a dye and a thickener. Among the commonly used thickeners are biological polymers and chemically modified biological polymers, such as alginate, starch or modified starch, locust bean gum, galactomannan or modified galactomannan and carboxymethyl cellulose.

With most printing methods, the polymer and excess dye must be removed by washing with water after the fixation of the print. Generally, a large amount of water is required for complete removal due to the high viscosity and low water solubility of the printing paste. Insufficient removal leads to unsatisfactory quality of the finished textile for the following reasons: 1) dye may be transferred to other parts of the printed textile or to other garments during laundering by the consumer. 2) Residual thickener will make printed areas stiff. It is the object of this invention to decrease process time as well as the amount of energy and water needed to achieve a satisfactory quality of the textile and to increase the quality which can be obtained regarding colour fastness and "hand".

STATEMENT OF THE INVENTION

We have now found that the removal of the thickener and excess dye can be made much more efficient by treating the printed textile with a suitable enzyme at the beginning of the wash. The enzymatic breakdown of thickener will decrease process time as well as the amount of energy and water needed to achieve a satisfactory quality of the textile.

Although the need for better removal has been recognized for decades and many of the enzymes of the type used in the invention have long been available, an enzymatic process has so far never been suggested.

Accordingly, the invention provides a method for removal of excess dye and biological polymer or chemically modified polymer from printed textile by washing, characterized by comprising treatment of the textile with an aqueous solution containing an enzyme that hydrolyses said polymer.

DETAILED DESCRIPTION OF THE INVENTION

Polymer (Thickener)

Figure 1:
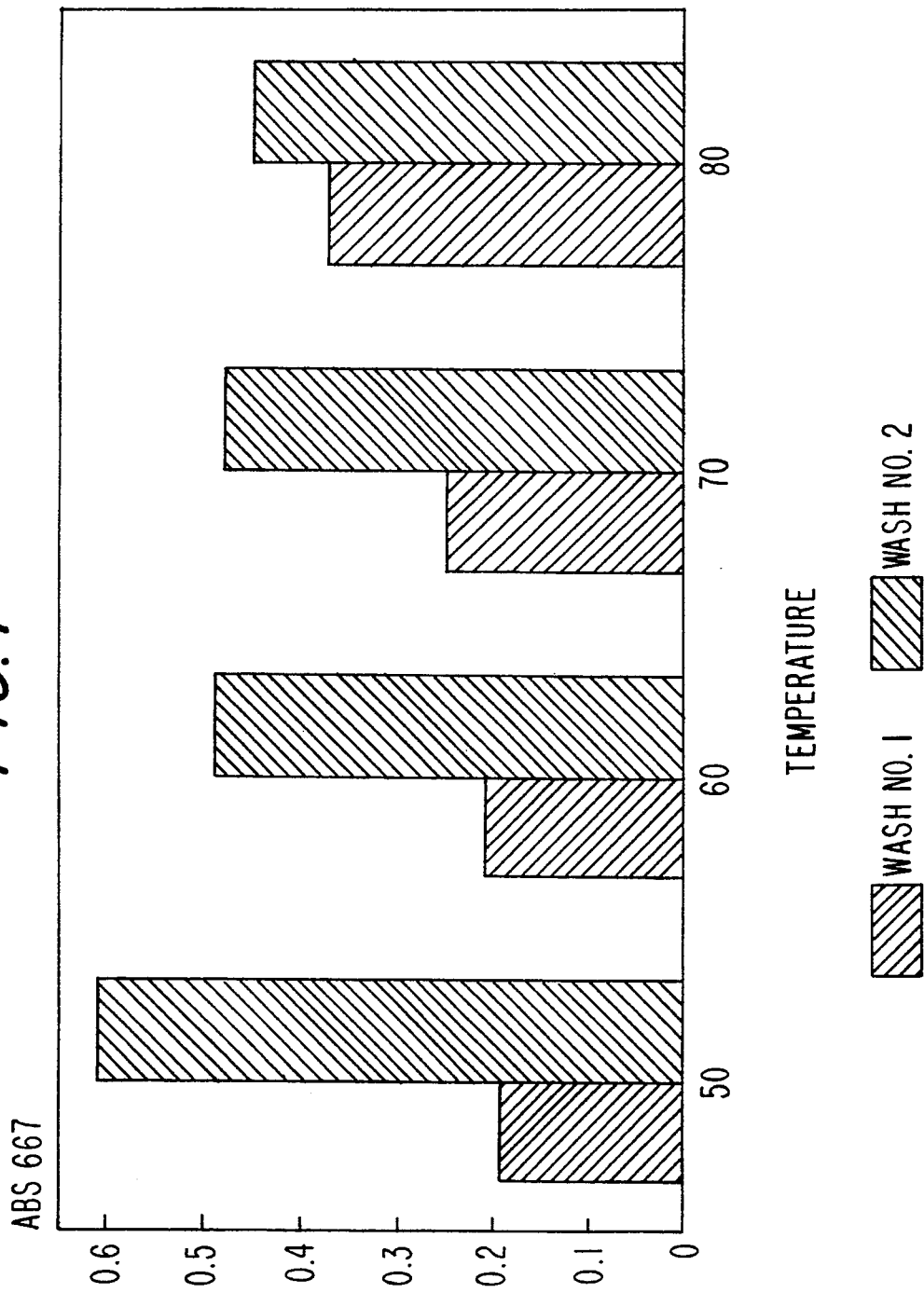
FIG. 1 shows the absorbance of the wash liquor after a first wash without enzyme addition.

Some examples of commonly used thickeners that may be treated according to the invention are alginate, a modified alginate, starch, a modified starch, a modified cellulose, carrageenan, laminarin, a galactomannan, a modified galactomannan, guar gum or locust bean gum, particularly triethanolalginate, etherified starch, esterified starch, ethoxylated starch, carboxymethyl starch, oxidized starch, cross-linked starch, ethoxylated galactomannan, carboxymethyl galactomannan, carboxyethyl galactomannan, carboxymethyl cellulose or carboxyethyl cellulose. It is noted that laminarin (1,3-$\beta$-D-glucan) may be present in commercial alginate products. In some circumstances thickeners are mixed e.g. alginate may be used together with starch, starch derivatives or carboxymethyl cellulose.

Textile

The process of the invention is applicable to all types of textile materials, both natural fibers (NF) and man-made fibers (MMF) as well as any combination hereof. Typical examples are cellulosic fibers (e.g. cotton and flax), cellulose fibers (e.g. acetate and triacetate), protein fibers (e.g. wool and silk), polyamide fibers (e.g. nylon 6 and 6,6), polyester fibers (e.g. polyethylene terephthalate) and acrylic fibers. The textile may be woven or knitted.

Printing Method

The process of the invention is suited for excess dye and polymer removal after any kind of printing with dyestuff. Examples of commonly used techniques are printing on a Rotation film, a Rouleaux, a Flash film, a Transfer film device.

Dyestuff

The process of the invention can be used for improved removal of any kind of dye, including synthetic and natural dyes. Typical printing dyes are those with anionic functional groups (e.g. acid dyes, direct dyes, Mordant dyes and reactive dyes), those with cationic groups (e.g. basic dyes), those requiring chemical reaction before application (e.g. vat dyes) and those chemically reacting with the fabric (e.g. reactive dyes) as well as sulphur dyes, disperse dyes and solvent dyes.

Enzyme

According to the invention, the type of enzyme is selected so that it can depolymerize the type of thickener being used. Microbial enzymes are preferred for reasons of economy. Endo-acting enzymes are preferred.

Thus, alginate lyase can be used to treat alginate and modified alginate. The alginate lyase may be derived from microbial strains of *Bacillus stearothermophilus* (e.g. NRRL B-18394 described in WO 90/02974), *Bacillus circulans* and *Klebsiella aerogenes.*

Starch and modified starch can be treated with amylase, e.g. derived from strains of Bacillus, particularly *B. amyloliquefaciens, B. licheniformis* or *B. stearothermophilus* or Aspergillus, particularly *A. oryzae* or *A. niger.*

Endo-1,4-$\beta$-D-mannanase (EC 3.2.1.78) can be used to treat galactomannans, guar gum and locust bean gum. This enzyme may be derived from Aspergillus, Humicola, or Tricoderma.

Carrageenanase (EC 3.2.1.83) may be used to treat carrageenan.

Modified cellulose can be treated with a cellulase, e.g. derived from Humicola, Tricoderma or Aspergillus. Advantageously, in the case of cellulose fibers the cellulase may be used to achieve softening of the textile simultaneously with the dye and thickener removal.

Laminarin may be treated with endo-1,3-$\beta$-D-glucanase (laminarinase, EC 3.2.1.39). Thus, alginate containing laminarin is preferably treated with alginate lyase together with laminarinase.

Process Conditions

In a conventional process the printed textile is first rinsed with cold water, then washed at high temperature with the addition of a detergent and sometimes also a suitable additive to decrease backstaining. The process is repeated until satisfactory amount of thickener and dyestuff have been removed. The enzyme treatment can be applied in one of the hot washes of the printed textile, preferably the first hot wash. The process may be run in batch mode or continuous mode. The process may be applied on a winch, a beck, a jet dyer, a jig, a open-width washing machine, a pad roll or any other equipment available suitable for a washing process or a incubation of the enzyme with the textile before washing. The conditions applied for enzymatic removal of excess thickener and dyestuff depend on the type of enzyme/thickener and the selected equipment.

The process conditions must be chosen according to the characteristics of the enzyme in question. They are generally in the range 20°–120° C., pH 3–11, typically 30°–90° C., pH 4–10 (or 4–9), especially 40°–80° C. (or 40°–75° C.), pH 5–9 (or 5.5–8.5).

EXAMPLES

In the examples that follow, all tested fabric samples were printed followed by fixation, but not rinsed or washed.

The polymer and unfixed dye (dye which is not fixed on/in the textile fibers itself) make up a coloured paste on and in between the textile fibers. When the thickener is hydrolyzed by the action of the enzyme it becomes more water soluble. The result is an increase of the velocity by which the polymer is removed from the textile surface into the solution.

Since the paste contains both polymer and unfixed dye, an increased solubilization velocity of the polymer will give an increased solubilization velocity of unfixed dyestuff. Thus, the amount of dye in solution is an indicator of the amount of thickener in solution.

EXAMPLE 1

Woven 100% cotton fabric were printed in stripes with an aqueous printing paste of the following composition:

6% Carboxymethyl galactomannan (Diagum CW-12)
15% Urea
2% Sodium bicarbonate
1% Ludigol (BASF, sodium nitrobenzene sulfonate)
3% Remazol turquoise blue G (reactive dye from Hoechst)

The fabric was cut into small pieces of 0.4 g all covered 100% with print paste whereafter they were rinsed together in excess cold water for 30 minutes. The pieces were added to two Erlenmeyer beakers each containing 20 g of buffer with the following composition: 1.8 mM citric acid, 6.4 mM orthophosphate, 60 ppm $Ca^{++}$, 1 g/l nonionic detergent (Sandopan DTC), pH 4.5. To each beaker 5 stainless steal balls (d=0.5 cm) were added. To one of the beakers 0.5 g/l of a freeze dried preparation of Endo-1,4-$\beta$-D-mannanase was added. Two different types of Endo-1,4-$\beta$-D-mannanase were tested: SP 496 (enzyme preparation from A. niger containing galactomannanase and cellulase) (1,400,000 VHCU/g) and SP 249 (enzyme preparation from A. aculeatus according to U.S. Pat. No. 4,478,939) (309,400 VHCU/g). The hot wash was performed at various temperatures with sealed beakers in a water bath for 30 minutes with a back and forth motion of 135 motions per minute.

The hot wash was repeated at 90° C. for 30 minutes without the addition of enzyme and with 1 g/l Tanaterge REM instead of Sandopan DTC at pH 4.5 with addition of 10 mM $MgCl_2$.

The fabric samples were rinsed cold in Miele washing machine between the two hot washes. The absorbance of the wash liquor after each wash was measured at 667 nm.

Figure 2:
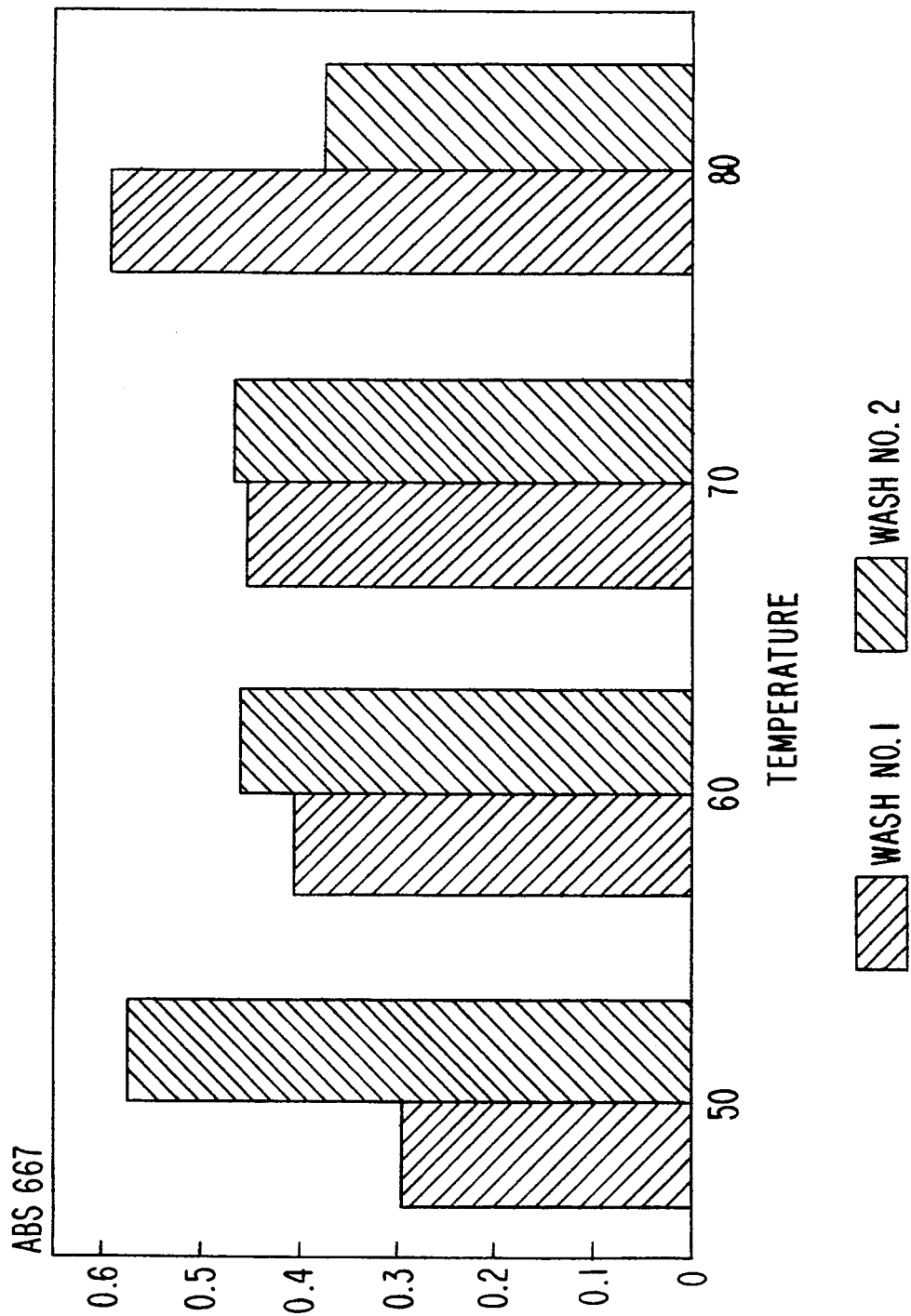
FIG. 2 shows the absorbance of the wash liquor after a first wash with SP 496 added.
Figure 3:
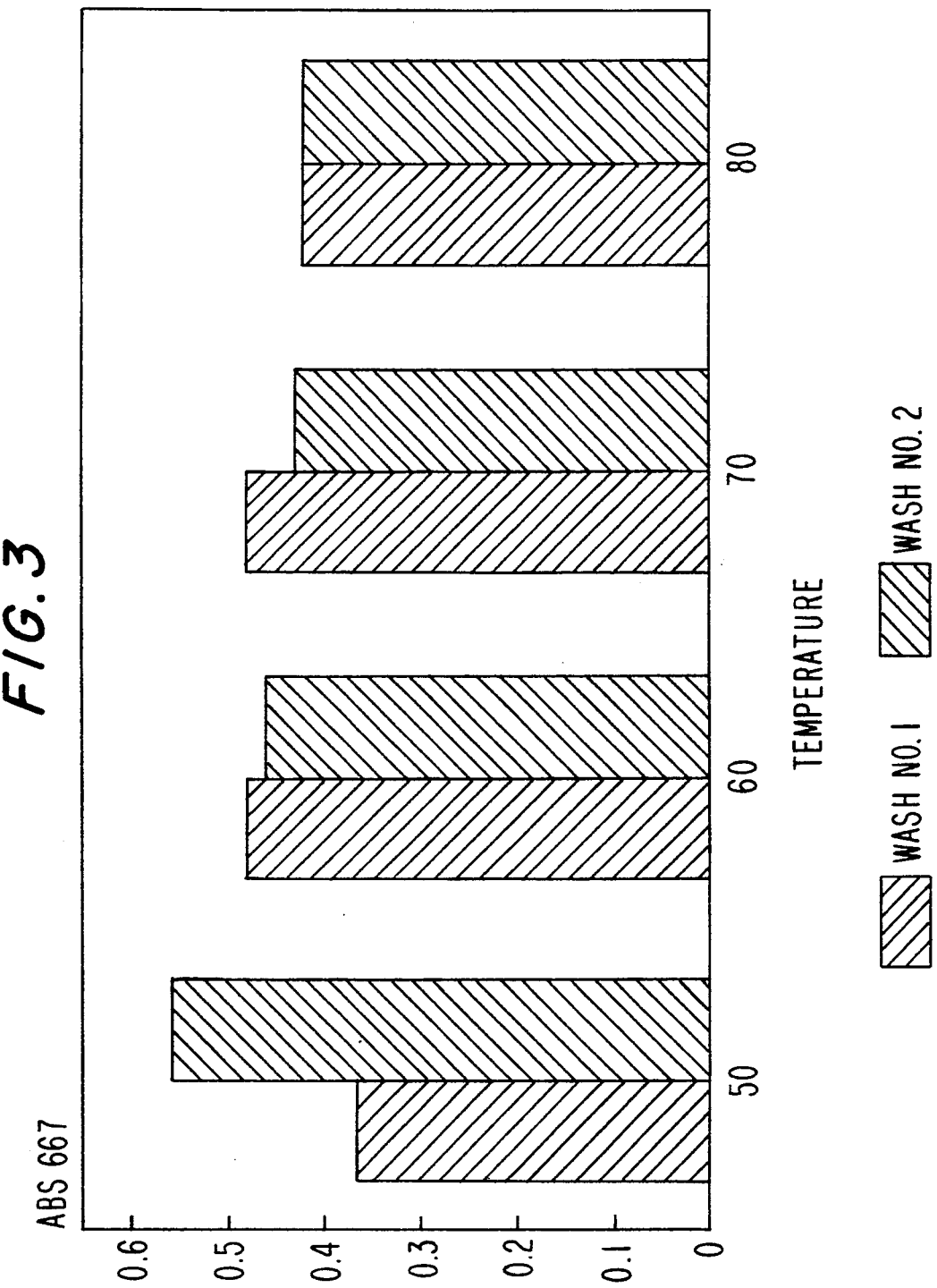
FIG. 3 shows the absorbance of the wash liquor after a first wash with SP 249 added.

The results are given in FIG. 1 (no enzyme addition in the first wash), FIG. 2 (0.5 g/l of SP 496 was added in the first wash) and FIG. 3 (0.5 g/l of SP 249 was added in the first wash).

An increase of dye release in the first wash was significant in all experiments. SP 496 is superior to SP 249 at high temperatures, whereas SP 249 is superior to SP 496 at low temperatures as can be seen from the graphs. A significant decrease of dye release is observed in the second hot wash in the case of SP 496, wash no 1 at 80° C.

EXAMPLE 2

Figure 4:
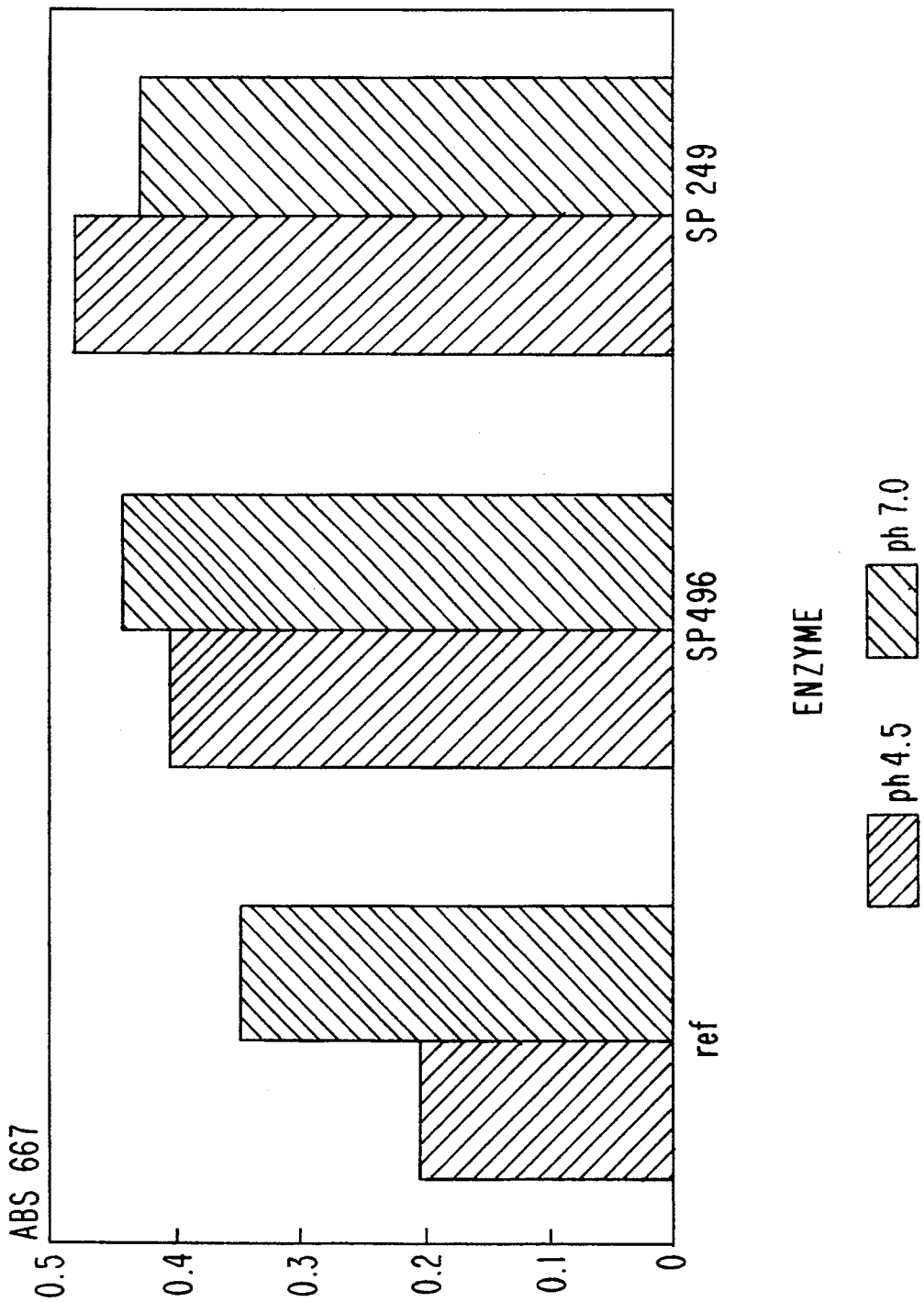
FIG. 4 shows the absorbance of the wash liquor after a first, hot wash and the effect of a pH adjustment.

All experimental condition were identical to Example 1. The effect of pH in the first hot wash was evaluated by adjusting the pH to 4.5 and 7, respectively. The absorbance of the wash liquor from the first hot wash is given in FIG. 4.

EXAMPLE 3

Woven 100% cotton fabric were printed in stripes with an aqueous printing paste with the same composition as in Example 1 except for the thickener. 15% starch derivative (Diatex SL) was used instead of 6% Carboxymethyl galactomannan (Diagum CW-12). The starch derivative is also know as British Gum (roasted starch).

The fabric was cut into small pieces of 0.4 g all covered 100% with print paste.

All experimental condition were identical to Example 1, except for the pH in the first wash, which was adjusted to 6.5 and the temperature of the first hot wash, which was 70° C. Instead of Endo-1,4-$\beta$-D-mannanase 3 g/l of three different commercial amylases were added to the first hot wash. Results were as follows.

|  | $ABS_{667}$ | |
| --- | --- | --- |
|  | Wash no 1 | Wash no 2 |
| No enzyme | 0.48 | 0.93 |
| Aquazyme 120 L | 2.23 | 0.15 |
| Aquazyme Ultra L | 2.30 | 0.15 |

-continued

| | ABS₆₆₇ | |
|---|---|---|
| | Wash no 1 | Wash no 2 |
| Termamyl 60 L | 2.37 | 0.17 |

EXAMPLE 4

Figure 5:
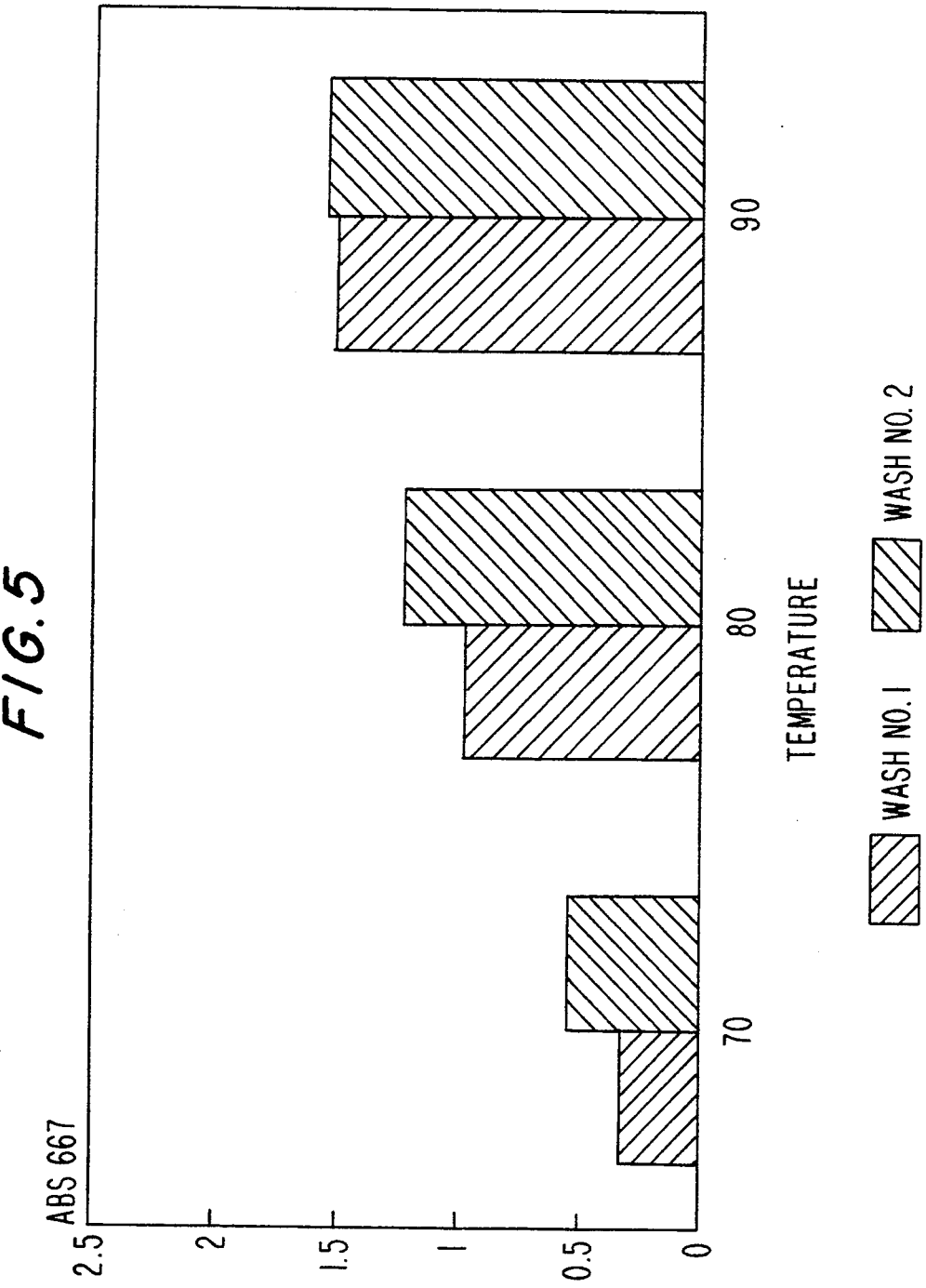
FIG. 5 shows the absorbance of the wash liquor after a first and a second hot wash with no additional enzyme.
Figure 6:
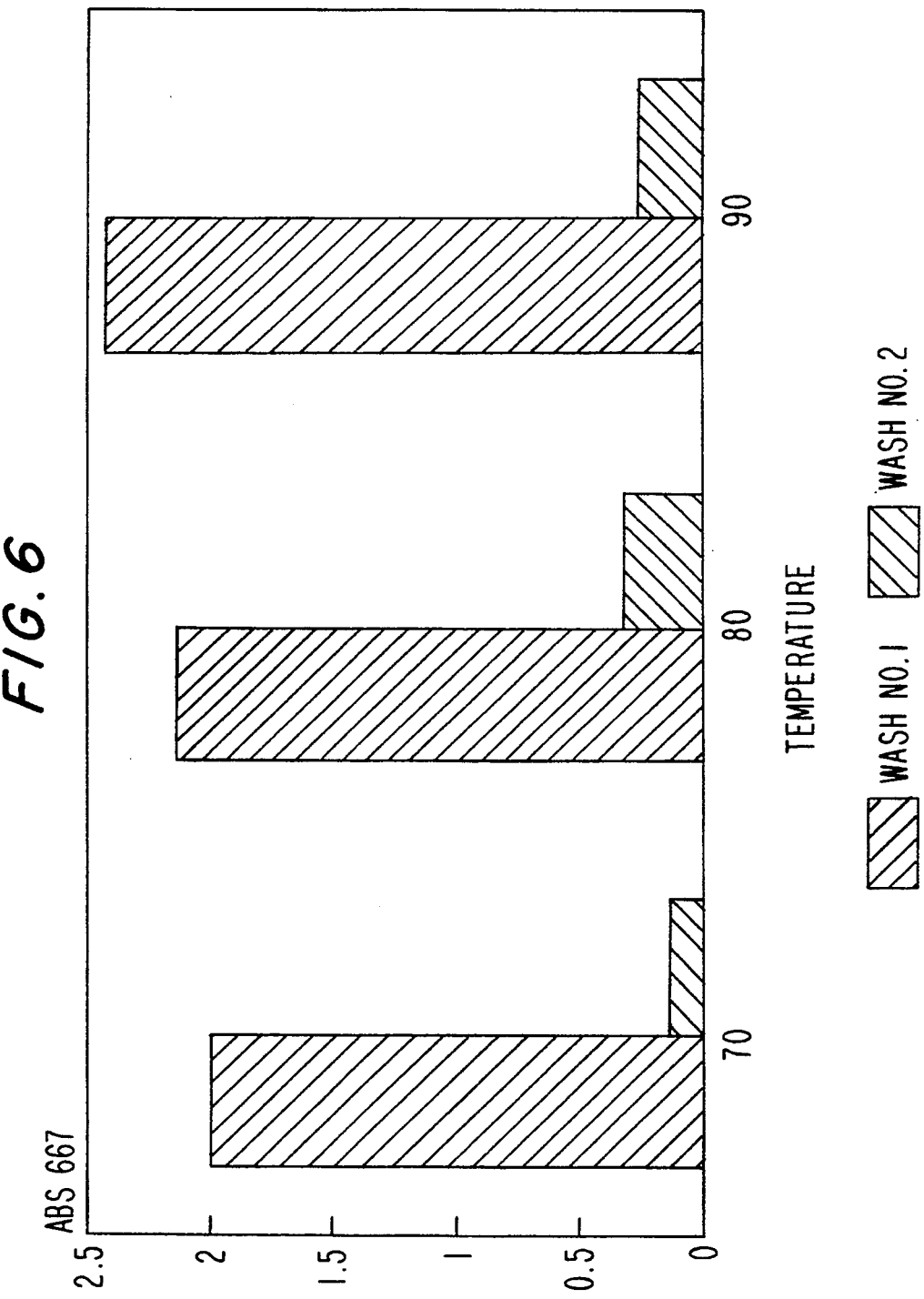
FIG. 6 shows the absorbance of the wash liquor after a two hot washes using Aquazyme Ultra.

All experimental condition were identical to Example 3. The effect of temperature in the first hot wash was evaluated on Aquazyme Ultra. The results are given in FIG. 5 (no addition of enzyme) and FIG. 6 (0.5 g/l Aquazyme Ultra).

EXAMPLE 5

Figure 7:
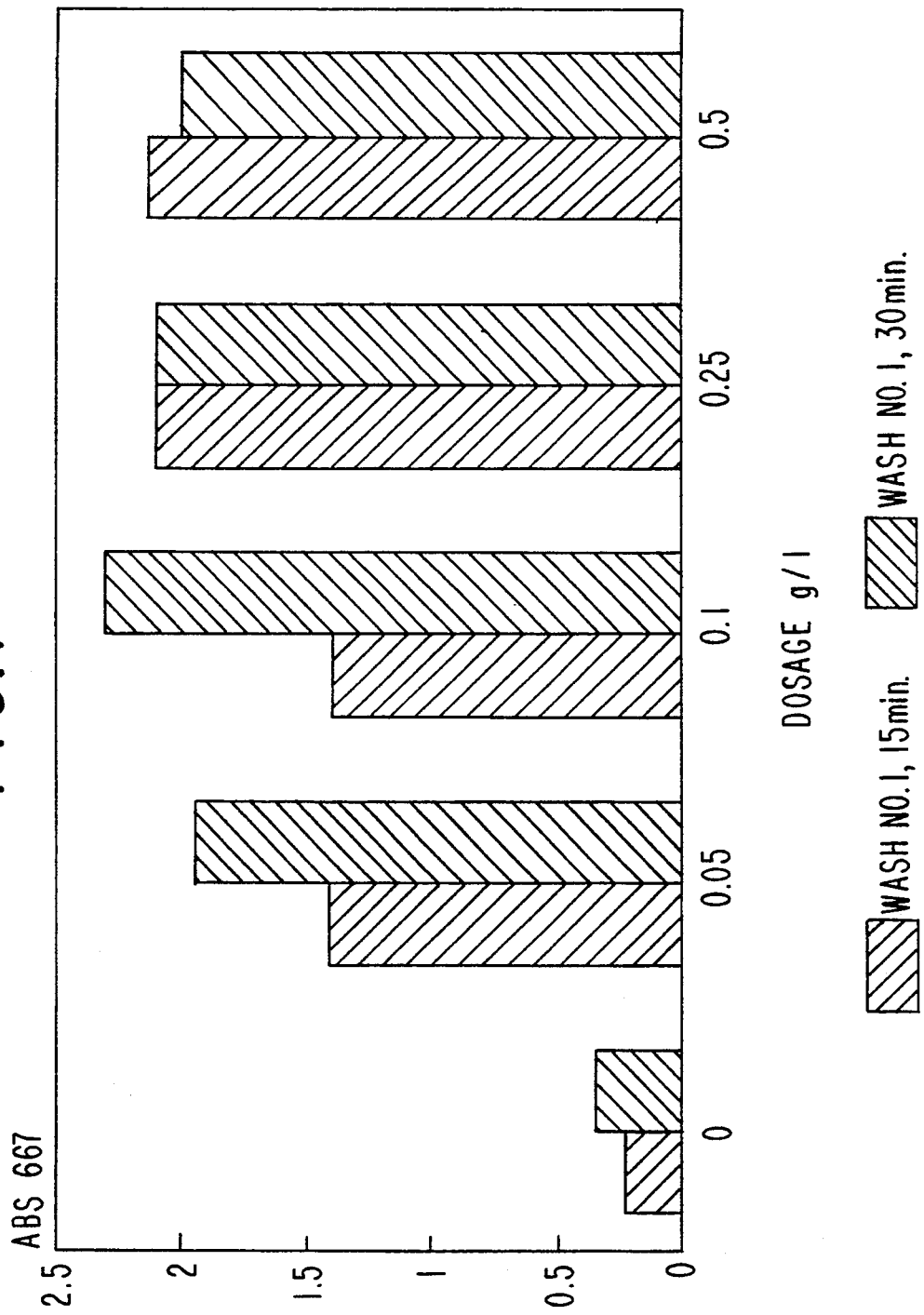
FIG. 7 (wash No. 1) and FIG. 8 (wash No. 2) show, with the absorbance readings, the effect of Aquazyme Ultra dosages on the first, hot wash liquors.
Figure 8:
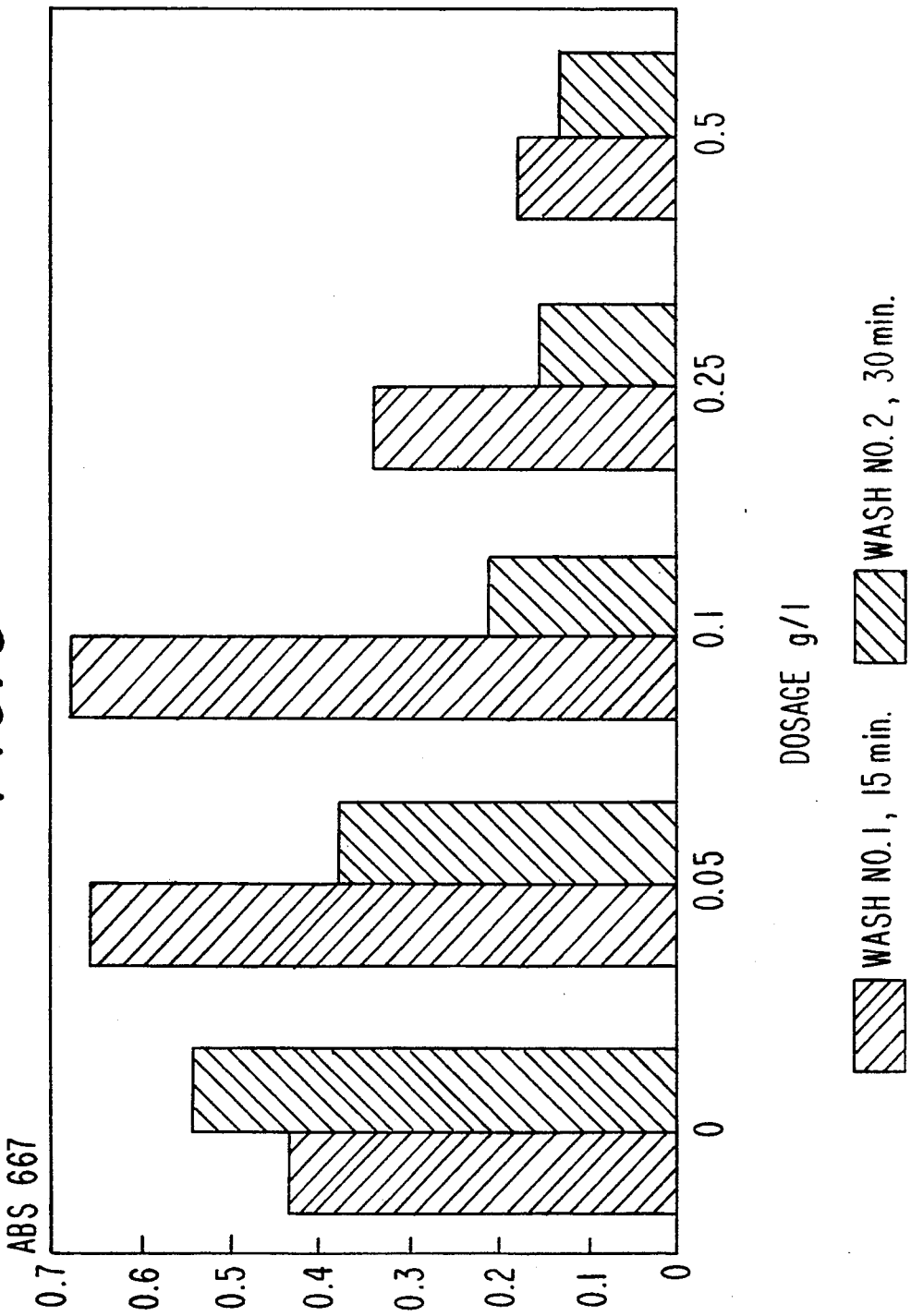

All experimental condition were identical to Example 3. The effect of Aquazyme Ultra dosage and time in the first hot wash at 70° C. was evaluated. Results are given in FIG. 7 (Wash no 1) and FIG. 8 (Wash no 2).

EXAMPLE 6

Woven 100% cotton fabric were printed in stripes with an aqueous printing paste with the same composition as in Example 1 except for the thickener. 3% highly substituted CMC (Diaprint 1060) was used instead of 6% Carboxymethyl galactomannan (Diagum CW-12).

The fabric was cut into small pieces of 0.4 g all covered 100% with print paste.

All experimental condition were identical to Example 1, except for the temperature in the first wash, which was 55° C. The cellulases listed below were all dosed 3 g/l in the first wash. SP 496 and SP 249 contain a cellulase with activity towards non-crystalline cellulose, whereas Cellusoft contains cellulases having activity towards both crystalline and non-crystalline cellulose. The activity of the enzyme preparation measured on CMC according to the analytical method described in WO 91/07542 is also listed in the following.

| | ABS₆₆₇ wash no 1 | Activity/g |
|---|---|---|
| No enzyme | 0.11 | |
| SP 496, CHN0009 | 0.13 | 9.51 EGU/g |
| SP 249, KRG0054 | 0.13 | 321 EGU/g |
| Cellusoft L, CCN3029 | 0.14 | 805 EGU/g |

EXAMPLE 7

A knitted fabric printed with a print paste containing sodium alginate as sole thickener and a red reactive dye was cut into small pieces of 0.500 g.

Two pieces covered 100% with print paste were rinsed together in excess cold water for 30 minutes. The pieces were added to two Erlenmeyer beakers each containing 20 g of buffer with the following composition: 1.8 mM citric acid, 6.4 mM orthophosphate, 60 ppm $Ca^{++}$, 10 mM $MgCl_2$, 1 g/l nonionic detergent (Sandopan DTC), pH 6.5. To each beaker 5 stainless steal balls (d=0.5 cm) were added. To one of the beakers 3 g/l of a freeze dried preparation of Alginate lyase from *Bacillus stearothermophilus* (NRRL B-18394) containing 250 U/g [Analytical method described in WO 90/02794].

The experiment was performed with sealed beakers in a water bath at 70° C. for 30 minutes with a back and forth motion of 135 motions per minute. The reaction was stopped by applying the pieces of fabric to a second cold rinse with excess water for 30 minutes.

The hot wash was repeated at 90° C. for 30 minutes without the addition of enzyme and with 1 g/l Tanaterge REM instead of Sandopan DTC.

The absorbance of the washing liquor at 510 nm (red colour) was measured after each wash. The colour removed in the intermediate rinse step was not measured. The results were as follows:

| | ABS₅₁₀ | |
|---|---|---|
| | Wash no 1 | Wash no 2 |
| No enzyme | 0.60 | 0.093 |
| Alginate lyase | 0.59 | 0.142 |

No effect on the alginate was seen in Wash No. 1 (where the enzyme was present). It is seen that the use of alginate lyase on knitted fabric increased the removal of colour and thickener in the non-enzymatic Wash No. 2.

EXAMPLE 8

Woven 100% cotton fabric were printed in stripes with an aqueous printing paste containing the following:

2% Alginate (Dialgin HV)
15% Urea
2% Sodium bicarbonate
1% Ludigol (BASF, sodium nitrobenzene sulfonate)
3% Remazol turquoise blue G (reactive dye from Hoechst)

After printing the fabric was fixed at 102° C. in saturated steam for 10 minutes. The fabric was cut into small pieces of 0.4 g all covered 100% with print paste.

The experimental conditions were as described in Example 7. The absorbance of the wash liquor after each wash was measured at 667 nm. Experiments were done in duplicates. The results were as follows:

| | ABS₆₆₇ | |
|---|---|---|
| | Wash no 1 | Wash no 2 |
| No enzyme | 2.00 | 4.66 |
| Alginate lyase | 2.00 | 2.18 |

As in the previous example, no effect on alginate was seen in Wash No. 1. It is seen that the use of alginate lyase on woven fabric led to less removal of colour and thickener in Wash No. 2, indicating increased removal in the rinsing step between the two washes (where colour was not measured).

We claim:

1. A method for treating a textile printed with a printing paste which comprises a dye and a biological or chemically modified polymer, said method comprising treating the textile with an aqueous solution comprising an enzyme, wherein the enzyme is an alginate lyase, an amylase, a cellulase, an endo-1,4-β-D-mannanase, a carrageenanase or an endo-1,3-β-D-glucanase modified cellulose, laminarin, a galactomannan, a modified galactomannan, guar gum, locust bean gum or carrageenan.

2. A method according to claim 1, wherein the polymer is triethanolalginate, etherified starch, esterified starch, oxidized starch, cross-linked starch, ethoxylated galactomannan, carboxymethyl galactomannan, carboxymethyl cellulose or carboxyethyl cellulose.

3. A method according to claim 1, wherein the textile is cellulosic, the polymer is a modified cellulose and the enzyme is a cellulase.

4. A method according to claim 1, wherein the polymer is an alginate or a modified alginate and the enzyme is an alginate lyase.

5. A method according to claim 1, wherein the polymer is a galactomannan or a modified galactomannan and the enzyme is an endo-1,4-$\beta$-D-mannanase.

6. A method according to claim 1, wherein the polymer is starch or a modified starch and the enzyme is an amylase.

7. A method according to claim 1, wherein the polymer is carrageenan or a modified carrageenan and the enzyme is a carrageenanase.

8. A method according to claim 1, wherein the polymer is laminarin and the enzyme is an endo-1,3-$\beta$-D-glucanase or a cellulase.

9. A method according to claim 1, wherein a mixture of polymers is used and the enzyme is able to hydrolyse one or all polymer component.

* * * * *